United States Patent [19]

Oliver et al.

[11] 4,061,591

[45] Dec. 6, 1977

[54] SELECTIVE ADSORBENT FOR USE IN AFFINITY CHROMATOGRAPHY

[75] Inventors: Roy Oliver, Rockford, Ill.; Garfield P. Royer, Worthington, Ohio

[73] Assignee: Pierce Chemical Company, Rockford, Ill.

[21] Appl. No.: 702,432

[22] Filed: July 6, 1976

Related U.S. Application Data

[63] Continuation of Ser. No. 507,197, Sept. 18, 1974, abandoned.

[51] Int. Cl.$^2$ ............................................. B01J 31/02
[52] U.S. Cl. ..................................... 252/430; 252/428
[58] Field of Search ........................ 252/426, 428, 430

[56] References Cited

PUBLICATIONS

Philipson et al., Proc. Nat. Acad. Sci. U.S.A., 68, pp. 2806–2809 (1971).

Sheldon et al., Proc. Nat. Acad. Sci. U.S.A., 69, pp. 417–421 (1972).

"Poly(U)–Sepharose 4B", Pharmacia Fine Chemicals AB, Jan. 1974.

*Primary Examiner*—W. J. Shine

[57] ABSTRACT

A new selective adsorbent for use in affinity chromatography. This adsorbent comprises, as one part, a water soluble covalently bonded complex of an affinity ligand and a biospecific handle. The other part thereof is an insoluble matrix or solid support which has covalently immobilized on its surface an adsorbent which has specific affinity for the biospecific handle of the complex. Attachment between the complex, containing the ligand, and the support is achieved by reversible coupling between the adsorbent and the biospecific handle and, as a result thereof, the ligand is not covalently bonded to the support. In turn, substantially complete recovery of the enzyme from the column can be effected.

5 Claims, No Drawings

SELECTIVE ADSORBENT FOR USE IN AFFINITY CHROMATOGRAPHY

This is a continuation of application Ser. No. 507,197, filed Sept. 18, 1974, now abandoned.

The present invention relates to the purification of enzymes and other proteins and, more particularly, to the use of affinity chromatography for this purpose.

As recognized by Cuatrecases (Advances in Enzymology, ed. Meister, Interscience, 1972), some conventional procedures for the purification of enzymes and other proteins depend on differences in the physicochemical properties of the various proteins present in a mixture. Since the differences are generally not unique, most of the available separation procedures of a preparative nature are not sufficiently indiscriminate to permit easy separation of molecules whose physicochemical differences are subtle.

Affinity chromatography, however, is a functional purification approach which exploits the most unique property of protein which is its biological specificity. For example, with respect to enzymes, there are active sites which perform two specialized functions. These functions are (1) recognition of restricted regions of other molecules and (2) catalysis of these restricted regions.

Affinity chromatography is based on function (1) wherein the active site of an enzyme can be used to recognize and bind to a selected region of a molecule for which the enzyme exhibits specific recognition. In basic respects, the existing methods of affinity chromatography involve preparation of a selective adsorbent by covalent immobilization of a molecule, containing the recognizable region, for which the protein to be separated is specific, to a suitable insoluble support. The immobilized compound is generally referred to as a ligand and it is recognized that coupling of the ligand to the support must be accomplished in a manner which does not interfere with its ability to be recognized by the enzyme. Affinity between ligand and the enzyme to be purified can be accomplished by passing the sample containing the enzyme through a column containing the selective adsorbent. Purification is thereafter accomplished by washing the column with a buffer used to free the adsorbent matrix of unwanted materials followed by elution of the adsorbed enzyme.

One problem encountered in conventional practice is that of achieving substantially complete elution of the protein without inactivating it. The enzyme is generally strongly bonded to the ligand and it is therefore difficult to remove it. Accordingly, it is an object of the present invention to provide an improved affinity chromatographic method for purifying a product wherein recovery of the purified product is easy to accomplish in good yield.

While the present invention will be described in connection with certain preferred embodiments, it is to be understood that it is not to be limited to only those embodiments. On the contrary, it is intended to cover all modifications and alternatives falling within the spirit and scope of the invention as expressed in the appended claims.

In one of its basic aspects, the present invention provides a new selective adsorbent for use in affinity chromatography. This adsorbent comprises, as one part, a water soluble covalently bonded complex of an affinity ligand and a biospecific handle. The other part thereof is an insoluble matrix or solid support which has covalently immobilized on its surface an adsorbent which has specific affinity for the biospecific handle of the complex. Attachment between the complex, containing the ligand, and the support is achieved by reversible coupling between the adsorbent and the biospecific handle and, as a result thereof, the ligand is not covalently bonded to the support. In turn, substantially complete recovery of the enzyme from the column can be effected.

Reversible coupling, for the instant purposes, is to be considered as attachment by means of a non-covalent and non-ionic association between two substances which have a specific affinity for each other in an aqueous medium, which affinity can be dissipated without chemical reaction. Reversible coupling thus permits attachment to and elution from the support without the use of harsh conditions which might adversely affect the protein to be purified.

Polynucleotides constitute a useful class of substances which can be employed as handles and adsorbents. These polymers are water soluble, can be immobilized on a support (Philipson et al. 1971, Proc. Nat. Acad. Sci. U.S.A. 68, 2806–2809 and Sheldon et al. 1972, Proc. Nat. Acad. Sci. U.S.A., 69, 417–421), and can be prepared with a sufficiently high molecular weight so as to provide firm anchoring of long polymer chains. With respect to these substances, coupling is effected through affinitive association between the base pairs of complementary polynucleotides. The coupling can be simply reversed by heat, or the institution of a competing association.

Representative examples, named as acids, of useful polynucleotides include polyadenylic acid, polyuridylic acid, polythymidylic acid, polycytidylic acid and polyguanylic acid. Preferably the acids have at least about ten repeating ribosephosphate moieties such as are commercially available. So as to achieve reversible coupling, the polynucleotide selected as the handle should have a base which is complementary, as to spatial arrangement and affinitive interaction, with the base of the polynucleotide adsorbent. Examples of useful complementary base pairs are adenine with either uracil or thymine and cytosine with guanine. Also, the 2' deoxy derivatives of the polynucleotides are preferably employed so as to minimize any reaction therewith during the purification procedure.

In further keeping with the present invention it has been indicated that a water insoluble support for the immobilized polynucleotide is employed. A variety of known water insoluble materials, either organic or inorganic, can be used. Porous glass beads constitute an especially preferred class of rigid supports. As hereinafter illustrated, these beads can be suitably derivatized and activated so as to effect immobilization of the polynucleotide thereon. Pierce Chemical Company of Rockford, Illinois, is a commercial source of such beads which are manufactured by Corning Works. A particularly useful support is "Glycophase" G porous glass beads. These beads are the 2, 3 dihydroxypropyloxypropyltrimethoxy silane derivative of porous glass.

The following example illustrates the present invention.

A. PREPARATION OF IMMOBILIZED POLYNUCLEOTIDE ADSORBENT

The arylamine derivative of "Glycophase" G porous glass beads (74–126 micron, pore diam. about 550° A), obtained from Pierce Chemical Co. of Rockford, Illinois, is prepared by reacting 10g of the beads with 0.5g para-nitrobenzyl bromide in 50 ml of dioxane for 24 hours at room temperature, followed by heating at 100° C. in a 10% aqueous solution of sodium dithionite.

The arylamine derivatized "Glycophase" G beads are washed with distilled water and are activated by diazotization in 30 ml of 0.5 n HCl at 0° C. with an excess of Na $NO_2$. After washing the activated beads with 3 liters of 3% sulfamic acid and 20 l of distilled water, the beads are reacted at 0° C. for 3 hours with 100 mg of commercial 2'-deoxypolyadenylic acid (MW – 1000) in buffer at pH8. After washing, the beads contain about 1%, by weight, of the acid. 30 grams of beads as so prepared are packed into a column equipped with a cooling jacket.

B. PREPARATION OF POLYNUCLEOTIDE-LIGAND COMPLEX 200 ml of degassed 0.1M phosphate buffer (pH 7.5) containing 1N. KCl is added to a reaction vessel followed by 200 mg. of commercial 2'-deoxypolythymidylic acid (Poly DT). The Poly DT has an average molecular weight of about 1000. The solution is maintained at a temperature of 25° C. and excess succinic anhydride is added. The resulting product is the 3' succinyl-Poly DT which is separated from solution and purified by passing the solution through the A column.

Bonding of the Poly DT to the ligand is then accomplished at 25° C. in water containing two equivalents of the hexamethylene derivative of the ligand NAD+, one equivalent of the succinyl derivatived Poly DT and 2 equivalents of 1, cyclohexyl-3 (2-morpholinoethyl-4-ethyl) carbodiimide. The NAD derivative is prepared as described by Craven et al., Febs. Letters, 38, 320 (1974). The complex, bonded through the $C_6$ position of the adinene ring and 3' position of the nucleotide terminal ribose moiety, is recovered in pure form as above.

C. PREPARATION OF SELECTIVE ADSORBENT

A solution of the complex from B, at 4° C., is passed by pumping at 5 ml/minute through the column containing the immobilized polyadenylic acid beads prepared in A. The column is then washed at 4° C. with 1 liter portions of water at 15 ml/min.

D. AFFINITY CHROMATOGRAPHY

An aqueous protein solution, containing an NAD+ specific enzyme is then passed through the column at 5 ml/min. and the column is then washed with 100 ml of water.

The complex, containing the affinity adsorbed protein is then eluted from the column with an aqueous solution at 40° C. A 5' nuclease is used to separate the polynucleotide handle from the NAD+ - protein system and the protein recovered by dialysis.

Alternatively, the protein solution can be first mixed with B. and the mixture then passed directly through the column.

Moreover, in effecting digestion with the 5' nuclease, this is preferably accomplished by passing the solution through a column containing the enzyme immobilized on the "Glycophase" G porous beads. A manner of effecting enzyme immobilization is described in Royer application, entitled "Molecular Transformation Procedure", filed on even date herewith.

We claim:
1. A selective adsorbent for use in affinity chromatography comprising, as one part, a water-soluble covalently bonded complex of an affinity ligand and a biospecific handle and, as the other part, an insoluble matrix or solid support which has covalently immobilized on its surface an adsorbent which has specific affinity for the biospecific handle of the complex, the biospecific handle and the absorbent being polynucleotides or 2' deoxy derivatives thereof, the polynucleotide of said handle having a base which is complementary, as to spatial arrangement and affinitive interaction, with the base of the polynucleotide adsorbent.

2. The selective adsorbent of claim 1 wherein the complementary base pairs are adenine with either uracil or thymine cytosine with guanine.

3. The selective adsorbent of claim 2 wherein the handle and absorbent are 2' deoxy derivatives of polynucleotides.

4. The selective adsorbent of claim 3 wherein the biospecific handle is 2'-deoxypolyadenylic acid.

5. The selective adsorbent of claim 4 wherein the insoluble matrix or solid support are porous glass beads.

* * * * *